US006977293B1

(12) United States Patent  (10) Patent No.: US 6,977,293 B1
Pennell  (45) Date of Patent: Dec. 20, 2005

(54) CHIMERIC POLYPEPTIDES

(75) Inventor: Roger I. Pennell, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 327 days.

(21) Appl. No.: 10/046,660

(22) Filed: Oct. 29, 2001

Related U.S. Application Data

(60) Provisional application No. 60/287,558, filed on Nov. 3, 2000.

(51) Int. Cl.$^7$ .......................... C07K 1/00; C12N 15/00; C12P 21/06
(52) U.S. Cl. .................... 530/350; 435/69.1; 435/320.1
(58) Field of Search ........................ 530/350; 435/69.1, 435/320.1, 252, 325; 536/23.1, 23.5

(56) References Cited

U.S. PATENT DOCUMENTS

| | | | |
|---|---|---|---|
| 4,851,341 A | 7/1989 | Hopp et al. | |
| 4,940,838 A | 7/1990 | Schilperoort et al. | |
| 5,011,912 A | 4/1991 | Hopp et al. | |
| 5,491,084 A | 2/1996 | Chalfie et al. | |
| 5,591,616 A | 1/1997 | Hiei et al. | |
| 5,625,048 A | 4/1997 | Tsien et al. | |
| 5,777,079 A | 7/1998 | Tsien et al. | |
| 5,968,793 A | 10/1999 | Liu et al. | |
| 6,017,734 A | 1/2000 | Summers et al. | |
| 6,306,373 B1 * | 10/2001 | Impernate et al. | ............ 424/59 |
| 2001/0044130 A1 * | 11/2001 | Glucksmann et al. | ...... 435/69.1 |

FOREIGN PATENT DOCUMENTS

| | | |
|---|---|---|
| WO | WO 97/30164 | 8/1997 |
| WO | WO 98/21938 | 5/1998 |
| WO | WO 00/34318 | 6/2000 |
| WO | WO 00/34319 | 6/2000 |
| WO | WO 00/34320 | 6/2000 |
| WO | WO 00/34321 | 6/2000 |
| WO | WO 00/34322 | 6/2000 |
| WO | WO 00/34323 | 6/2000 |
| WO | WO 00/34324 | 6/2000 |
| WO | WO 00/34325 | 6/2000 |
| WO | WO 00/34326 | 6/2000 |
| WO | WO 00/34526 | 6/2000 |

OTHER PUBLICATIONS

GenBank Accession No. S74033.
Bechtold et al., "In planta Agrobacterium mediated gene transfer by infiltration of adult *Arabidopsis thaliana* plants," *C.R. Acad. Sci. Paris*, 1993, 316:1194–1199.
Buchanan, "β–Barrel proteins from bacterial outer membranes; structure, function and refolding," *Curr. Opin. Struct. Biol.*, 1999, 9:455–461.
Fasman and Gilbert, "The prediction of transmembrane protein sequences and their conformation: an evaluation," *TIBS*, 1990, 15:89–92.

Garavito and White, "Membrane proteins—Structure, assembly, and function; a panoply of progress," *Curr. Opin. Struct. Biol.*, 1997, 7:533–536.
Gietz and Woods, "Transformation of Yeast by the Lithium Acetate/Single–Stranded Carrier DNA/PEG Method," *Methods in Microbiology*, 1998, 26:53–66.
Hirasawa et al., "Subtype–Specific Differences in Subcellular Localization of $\alpha_1$–Adrenoceptors Irrespective of the Subtype," *Mol. Pharmacol.*, 1997, 52:764–770.
Klein et al., "The detection and classification of membrane–spanning proteins," *Biochim. Biophys. Acta*, 1985, 815:468–476.
Lange et al., "Probing essential oil biosynthesis and secretion by functional evaluation of expressed sequence tags from mint gladular trichomes," *PNAS*, 2000, 97(6):2934–2939.
Lesieur et al., "Membrane insertion: the strategies of toxins," *Mol. Mem. Biol.*, 1997, 14:45–64.
Li et al., "Generation of Destabilized Green Fluorescent Protein as a Transcription Reporter," *J. Biol. Chem..*, 1998, 273(52):34970–34975.
Lio and Vannucci, "Wavelet change–point prediction of transmembrane proteins," *Bioinformatics*, 2000, 16(4):376–382.
"Living Colors® User Manual," Clontech, Apr. 1999, PT2040–1, version PR94845, pp. 1–51 (and Addendum).
"Living Colors® User Manual," Clontech, Oct. 1999, PT3404–1, version PR9X217, pp. 1–19.
Lu et al., "AtMRP2, an Arabidopsis ATP Binding Cassette Transporter Able to Transport Glutathione S–Conjugates and Chlorophyll Catabolites: Functional Comparisons with AtMRP1," *Plant Cell*, 1998, 10:267–282.
Luo et al., "Expression and parent–of–origin effects for *FIS2*, *MEA*, and *FIE* in the endosperm and embryo of developing *Arabidopsis* seeds," *PNAS*, 2000, 97(19):10637–10642.
Mai and Breeden, "*CLN1* and Its Repression by Xbp1 Are Important for Efficient Sporulation in Budding Yeast," *Mol. Cell. Biol.*, 2000, 20(2):478–487.
Masucci et al., "The homeobox gene *GLABRA 2* is required for position–dependent cell differentiation in the root epidermis of *Arabidopsis thaliana*," *Development*, 1996, 122:1253–1260.

(Continued)

*Primary Examiner*—Jon Weber
*Assistant Examiner*—Sheridan Snedden
(74) *Attorney, Agent, or Firm*—Fish & Richardson P.C., P.A.

(57) ABSTRACT

A new class of chimeric polypeptides is disclosed that includes a transmembrane segment, an intracellular reporting segment, and an extracellular sorting segment. The novel polypeptides can be used to detect gene expression at the cellular level, and to isolate precisely those cells that are detected from organisms, organs, tissues, and mixtures of cells.

14 Claims, No Drawings

OTHER PUBLICATIONS

McCabe et al., "Soluble Signals from Cells Identified at the Cell Wall Establish a Developmental Pathway in Carrot," *Plant Cell*, 1997, 9:2225–2241.

Meera et al., "Large conductance voltage– and calcium–dependent K$^+$channel, a distinct member of voltage–dependent ion channels with seven N–terminal transmembrane segments (S0–S6), an extracellular N terminus, and an intracellular (S9–S10) C terminus," *PNAS*, 1997, 94:14066–14071.

Rideout III et al., "Generation of mice from wild–type and targeted ES cells by nuclear cloning," *Nature Genetics*, 2000, 24:109–110.

Schulz, "Porins: general to specific, native to engineered passive pores," *Curr. Biol. Struct. Biol.*, 1996, 6:485–490.

Schulz, "β–Barrel membrane proteins," *Curr. Opin. Struct. Biol.*, 2000, 10:443–447.

Schwarz et al., "Spatial specification of mammalian eye territories by reciprocal," *Development*, 2000, 127:4325–4334.

Smith et al., "A dominant mutation in the maize homeobox gene, *Knotted–1*, causes its ectopic expression in leaf cells with altered fates," *Development*, 1992, 116:21–30.

Ye et al., "Engineering the Provitamin A (β–Carotene) Biosynthetic Pathway to (Carotenoid–Free) Rice Endosperm," *Science*, 2000, 287:303–305.

Yellin et al., "EmrE, a Small *Escherichia coli* Multidrug Transporter, Protects *Saccharomyces cerevisiae* from Toxins by Sequestration in the Vacuole," *J. Bacteriol.*, 1999, 181(3):949–956.

\* cited by examiner

CHIMERIC POLYPEPTIDES

CROSS-REFERENCE TO RELATED APPLICATIONS

This application claims priority from U.S. Provisional Application Ser. No. 60/287,558, filed on Nov. 3, 2000.

TECHNICAL FIELD

The present invention relates generally to methods and materials useful for profiling gene expression at the cellular level and for isolating specific cells. Specifically, the invention pertains to chimeric polypeptides useful for identifying genes expressed in specific cells, identifying genetic regulatory elements in specific cells, and isolating specific cells from organisms or mixtures of cells.

BACKGROUND

Academic and commercial researchers have long recognized that the analysis of gene expression is important for modifying physiological processes, for developing new or improved therapies, or for improving biological products. It is extremely difficult and time-intensive, if not altogether impossible to identify genetic regulatory elements and construct profiles of expressed genes in specific cells using traditional methods of genetic analysis.

SUMMARY

The invention is based on a new class of chimeric polypeptides that can be used in a variety of research and clinical settings to identify genes expressed in specific cells, to identify regulatory elements important for gene expression in specific cells, and to isolate specific cells from organisms or mixtures of cells. These novel chimeric polypeptides include a transmembrane segment, an intracellular reporting segment, and an extracellular sorting segment.

The present invention allows researchers to detect gene expression at the cellular level, and to isolate precisely those cells that are detected from organisms, organs, tissues, and mixtures of cells. Detection and isolation can be accomplished simultaneously, and without multiple cloning steps. Using the present invention, scientists can identify specific cells by detecting gene expression in specific cells and can isolate these specific cells from others in an organism or mixture of cells. Thus, the invention is useful for isolating specific cells. Scientists can study the isolated cells to identify genetic regulatory elements important for gene expression in specific cells. Scientists can also construct cDNA libraries from the isolated cells to identify genes that are expressed in specific cells (i.e., construct cell-specific gene expression profiles).

The present invention features chimeric polypeptides having at least one transmembrane segment, a sorting segment positioned within an extracellular domain of the chimeric polypeptide, and an intracellular reporting segment. A sorting segment is positioned at other than the amino terminus of a chimeric polypeptide. In some embodiments, a chimeric polypeptide has two or more transmembrane segments, and an extracellular domain in such a chimeric polypeptide can be positioned in an extracellular loop. In some embodiments, a reporting segment is positioned at the carboxy terminus and/or at the amino terminus of a chimeric polypeptide.

In some embodiments, a chimeric polypeptide contains a c-myc, FLAG, 6×HIS, Hemagglutinin, avidin and/or streptavidin sorting segment. Chimeric polypeptides according to the present invention can have a bioluminescent reporting segment. In some embodiments the reporting segment fluoresces upon exposure to ultraviolet or visible light having a wavelength between 300 nm and 600 nm. In some embodiments, the reporting segment is amFP486, asFP600, cFP484, dgFP512, dmFP592, drFP583, drFP583/dmFP592, dsFP483, zFP506, zFP538, GFP, GFPuv, GFPmutl, EGFP, ECFP, EYFP, EBFP, BFP2, d4EGFP, d2EGFP, d1EGFP, d4EGFP, DsRed, or DsRed1. In some embodiments, the reporting segment is capable of enzymatic catalysis.

The present invention also features nucleic acids that encode a chimeric polypeptide, and nucleic acid constructs that have a promoter operably linked to a sequence that encodes a chimeric polypeptide. The invention also features cells containing a chimeric polypeptide, cells containing a nucleic acid that encodes a chimeric polypeptide, and cells containing a nucleic acid construct having promoter that is operably linked to a sequence that encodes a chimeric polypeptide.

The invention also features methods for isolating specific cells, involving 1) detecting specific cells in a transgenic organism that expresses a chimeric polypeptide by detecting the presence of the reporting segment in the specific cells, and 2) isolating the specific cells by using the sorting segment of the chimeric polypeptide. These methods can also be used to isolate specific cells from a mixture of cells. In some embodiments, transgenic organisms or mixtures of cells employed in these methods comprise two nucleic acid constructs. The first nucleic acid construct includes a first promoter, at least one transcription activator binding sequence operably linked to the first promoter, and a first coding sequence encoding a chimeric polypeptide that is operably linked to the first promoter and to the transcription activator binding sequence. The second nucleic acid construct includes a second promoter operably linked to a second coding sequence encoding a transcriptional activator polypeptide that has a DNA binding domain and a transcription activation domain. In some embodiments, the first promoter is a minimal promoter.

The invention also features methods for isolating specific cells, involving 1) providing a population of transgenic organisms, a plurality of which contain a nucleic acid construct having promoter that is operably linked to a sequence that encodes a chimeric polypeptide, 2) identifying the specific cells within at least one transgenic organism in said plurality that express a chimeric polypeptide by detecting the presence of the reporting segment in the specific cells, and 3) isolating the specific cells by using the sorting segment of the chimeric polypeptide. These methods can also be used to isolate specific cells from a population of cells. In some embodiments, the population of cells includes two or more different specific cells. In some embodiments, the population of cells is an organ, organ sample, tissue, or tissue sample. In some embodiments, the transgenic organisms or populations of cells employed in these methods contain two nucleic acid constructs: a first nucleic acid construct includes a first promoter, at least one transcription activator binding sequence operably linked to the first promoter, and a first coding sequence encoding a chimeric polypeptide that is operably linked to the first promoter and to the transcription activator binding sequence; and a second nucleic acid construct includes a second promoter operably linked to a second coding sequence encoding a transcriptional activator polypeptide that has a DNA binding domain and a transcription activation domain. In some embodiments, the first promoter is a minimal promoter Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention features techniques for profiling gene expression in specific cells and for isolating specific cells from organisms or mixtures of cells. These methods use a new class of chimeric polypeptides that include a transmembrane segment, an intracellular reporting segment, and an extracellular sorting segment.

Chimeric polypeptides.

The chimeric polypeptides featured in this invention include one or more transmembrane segments, an intracellular reporting segment, and an extracellular sorting segment. Such polypeptides are chimeric in the sense that they are arranged in a configuration not normally found in nature. For example, the amino acid sequence of one or more of the segments can be a non-naturally occurring sequence. As another example, the amino acid sequence of one segment may be a naturally occurring sequence found in one species, whereas the amino acid sequences of remaining segments may be naturally occurring sequences from different species or from-different alleles of the same species. Segments of polypeptides are contiguous chains of at least 2 amino acids that can include any naturally occurring amino acid or derivative thereof Chimeric polypeptides can include any naturally occurring amino acid or derivative thereof To be suitable as a transmembrane, reporting, or sorting segment of a chimeric polypeptide, the biological activity of some amino acid sequences might need to be disabled to prevent disruption of vital cellular functions or gene expression profiles in specific cells. For example, the biological activity of some naturally occurring transmembrane polypeptides (e.g. ion channels or porins) might have to be eliminated (e.g., by amino acid deletion or substitution). One or more transmembrane segments of a naturally occurring polypeptide that are not associated with the biological activity of the polypeptide (e.g., ion translocation) can be excised and assembled into a chimeric polypeptide.

Chimeric polypeptides span a membrane or a lipid bilayer, and thus have one or more extracellular domains and one or more intracellular domains. An extracellular domain includes amino acids situated outside the volume defined by the membrane that the chimeric polypeptide traverses, and contains one or more sorting segments. A sorting segment can be located anywhere within an extracellular domain, except that when the extracellular domain is positioned at the N-terminus of the polypeptide, there is at least one amino acid between the N-terminus and the first amino acid of the sorting segment, e.g., two or more, three or more, ten or more, twenty or more, or fifty or more amino acids between the N-terminus and the first amino acid of the sorting segment. Typically, at least one sorting segment is positioned in an extracellular loop between two transmembrane segments.

An intracellular domain includes amino acids situated inside the volume defined by the membrane that the chimeric polypeptide traverses, and contains at least one reporting segment. A reporting segment can be positioned anywhere within an intracellular domain. Typically, however, a reporting segment is positioned at the C-terminus of the chimeric polypeptide when the C-terminus is part of an intracellular domain, which facilitates construction of nucleic acids encoding such a polypeptide.

Each intracellular domain and extracellular domain of a chimeric polypeptide are separated by at least one transmembrane segment. A transmembrane segment is a polypeptide segment that spans a biological membrane such as a plasma membrane, organelle membrane, or lipid bilayer. A transmembrane segment can have an α-helix or β-strand backbone conformation. A transmembrane segment can be obtained from a naturally occurring membrane-spanning polypeptide or can be non-naturally occurring consensus sequence. Naturally occurring polypeptides that contain α-helix transmembrane segments include, for example: bacteriorhodopsin; photosynthetic reaction center L- and M-chains; cytochrome c oxidase; F1F0 ATP synthase C and A subunits; cytochrome bc1; Kcsa; fumarate reductase; exotoxin A; diptheria toxin; Cry δ-endotoxin; colicins A, El, Ia, and N. Naturally occurring polypeptides that contain β-strand transmembrane segments include, for example: OmpF; OmpA; PhoE; OmpX; OmpLA; FhuA; FepA; LainB; aerolysin; a-toxin; anthrax toxin; Cry δ-endotoxin; pneumolysin and streptolysin. Amino acid sequences for the above-mentioned naturally occurring polypeptides can be found in Genbank. Synthetic transmembrane segments can be designed on the basis of the amino acid sequence of known transmembrane segments. Transmembrane segments can be identified by a variety of predictive methodologies. Lio and Vannucci describe an exemplary predictive method (see Bioinformatics 16:376–382. 2000). Freely available WaveThresh3 software can be used in conjunction with the widely used S-Plus statistical software to perform the method of Lio and Vannucci. Many transmembrane segments can also be identified by the presence of associated amino-terminal signal sequences. Transmembrane segments can also be identified by routine experimental techniques for cell fractionation and polypeptide localization.

A sorting segment is a polypeptide segment that can be used to isolate a specific cell type in which the chimeric polypeptide is expressed. Sorting segments often bind to, have affinity for, or can be coupled with another molecule such that chromatographic or batchwise separation techniques can be used to carry out such isolation. For example, a sorting segment can bind to or have affinity for molecules such as antibodies, avidin or streptavidin. Sorting segments include, for example: FLAGS™(U.S. Pat. No. 4,851,341); 6×HIS; c-myc; Protein C; VSV-G; Hemagglutinin and biotin. Two or more sorting segments can be used in the same polypeptide.

A reporting segment is a polypeptide segment that permits detection of the presence of the chimeric polypeptide in situ or in vivo, either directly or indirectly, without affecting the ability to subsequently isolate the cell or cells in which the chimeric polypeptide is expressed. Typically, cells that express the chimeric polypeptide remain viable after detection of the reporting segment. For example, a reporting segment can itself be bioluminescent upon exposure to light. As an alternative, a reporting segment can catalyze a chemical reaction in vivo that yields a detectable product that is localized inside or that is associated with a cell that expresses the chimeric polypeptide. Exemplary bioluminescent reporting segments that emit light in the presence of additional polypeptides, substrates or cofactors include firefly luciferase and bacterial luciferase. Bioluminescent reporting segments that fluoresce in the absence of additional proteins, substrates or cofactors when exposed to light having a wavelength in the range of 300 nm to 600 nm include, for example: amFP486, Mut15-amFP486, Mut32-amFP486, CNFP-MODCd1 and CNFP-MODCd2 (WO 00/34320); asFP600, mut1-RNFP, NE-RNFP, d1RNFP and d2RNFP (WO 00/34319); cFP484, Δ19-cFP484 and Δ38-cFP484 (WO 00/34321); dgFP512 (WO 00/34323); dmFP592 (WO 00/34324); drFP583, E5 drFP583, E8 drFP583, E5UP drFP583, E5down drFP583, E57 drFP583, AG4 drFP583 and AG4H drFP583 (WO 00/34326); drFP583/dmFP592, drFP583/dmFP592-2G and drFP583/dmFP592-Q3 (WO 00/34326); dsFP483(WO 00/34322); zFP506, N65M-zFP506, dlzFp506 and d2zFP506 (WO 00/34318); zFP538, M128V-zFP538, YNFPM128V-MODCd1 and YNFPM128V-MODCd2, (WO 00/34325); GFP (GenBank Accession No. AAB57606); EGFP, ECFP, EYFP, EBFP, BFp2 (Clontech User Manual, Apr. 1999, PT2040-1, version PR94845; U.S. Pat. No. 5,777,079); d4EGFP, d2EGFP and d1EGFP (Clontech User Manual, Apr. 1999, PT2040-1, version PR94845; Li et al., *J Biol Chem* 1998, 273:34970–5); and DsRed and DsRed1 (Clontech User Manual, Oct. 1999, PT34040-1, version PR9X217). Reporting segments that catalyze a chemical reaction that yields a detectable product include, for example, β-galactosidase or β-glucuronidase.

The invention also features nucleic acid molecules encoding these chimeric polypeptides, cells containing these nucleic acids, and cells expressing these chimeric polypeptides.

Method for isolating specific cells.

The invention provides methods for isolating specific cells from a transgenic organism that expresses a chimeric polypeptide in those cells. The invention also provides a method for isolating specific cells from a mixture of cells that express the chimeric polypeptide. The term "specific cells" refers to cells that have one or more characteristics that distinguish them from the other cells in an organism, or from other cells in a mixture of cells. Distinguishing features can include, for example, physical location, cell division rate, developmental stage, differentiation status, macromolecular composition, gene expression profile, protein expression profile, particular cell type, or presence or absence of a particular polypeptide. Transgenic organisms can be animals, plants, and fungi. Suitable transgenic animals include insects, and non-human mammals such as mice, rats, sheep, cows and pigs. Suitable transgenic plants can be monocotyledonous or dicotyledonous plants, and include corn, soybeans, wheat, rice, rapeseed, sunflowers, and *Arabidopsis thaliana*. In some embodiments, specific cells are found in a single organ, tissue, or tissue or cell culture, e.g., egg cells from embryo sacs, scutellar cells of a mature kernel, cells containing seed storage proteins from cotyledons and rapidly dividing fibroblasts from skin. In other embodiments, specific cells are found in more than one organ, tissue, or tissue or cell culture, e.g., meristematic cells from plant shoot and root apices, and mucosal cells from the large intestine and the nasal cavity.

A specific cell that expresses a chimeric polypeptide is detected by the presence of the reporting segment. For example, transgenic organisms or mixtures of cells can be examined under light having a wavelength that causes a bioluminescent reporting segment to fluoresce. Alternatively, transgenic organisms or mixtures of cells can be examined after being exposed to the substrate of a reporting segment that catalyzes a chemical reaction to yield a detectable product.

The sorting segment is used to isolate a specific cell from a transgenic organism or mixture of cells that express the chimeric polypeptide in that cell. Use of the sorting segment can involve processing cells to expose the sorting segment. Exposure of a sorting segment may require excision or disruption of tissues and/or organs. For plant cells, removal of cell walls may be, but is not necessarily, required to facilitate isolation (see, e.g., McCabe et al. Plant Cell 9:2225–2241. 1997.).

An exposed sorting segment is contacted with a collecting molecule that the sorting segment binds to, has affinity for, or can be coupled to. For example, cells having an immunogenic sorting segment can be contacted with a collecting molecule such as a cognate antibody. Alternatively, cells having a biotinylated sorting segment can be contacted with streptavidin. Isolation of a specific cell can be facilitated by, for example, immobilizing collecting molecules on a solid substrate, attaching collecting molecules to paramagnetic beads, or reacting collecting molecules with a secondary antibody. It is contemplated that specific cells, after isolation from a transgenic organism or mixture of cells, can be enriched compared to their proportion prior to isolation by a factor ranging from $10^3$ to $10^7$ (e.g., $10^3$ to $10^4$, $10^4$ to $10^5$, $10^5$ to $10^6$, or $10^6$ to $10^7$).

Transgenic organisms or cells that express a chimeric polypeptide contain a nucleic acid construct in which a nucleic acid encoding a chimeric polypeptide is operably linked to a promoter. A promoter is a polynucleotide segment at which the process of transcription is initiated. Promoters can comprise one or more nucleotide subsegments that serve as recognition sites for RNA polymerase (RNAP). A promoter can be naturally present in a transgenic organism or cell, or can be introduced into the genome of the transgenic organism or cell. In some embodiments, the promoter can be a minimal promoter (i.e., a promoter that comprises one or more relatively poor recognition sites for RNAP and consequently serves as a relatively poor site for transcription initiation).

In some embodiments, a transgenic organism to be subjected to the method is selected from a population of transgenic organisms, some members of the population expressing the chimeric polypeptide in specific cells and other members not expressing the polypeptide. Similarly, in some embodiments, a mixture of cells subjected to the method are selected from a population of cells in which specific cells express the chimeric polypeptide and other cells do not.

A population of transgenic organisms or cells can be screened by observing the presence of the reporting segment to identify cells that express the chimeric polypeptide, or transgenic organisms that express the chimeric polypeptide in a cell-specific manner. The population of transgenic organisms or cells can be, for example, a collection of organisms or cells produced by transformation, transfection, or genetic crossing. Cells that express the chimeric polypeptide are specific cells in this context.

In some embodiments, a nucleic acid construct that encodes a chimeric polypeptide contains a recognition site for a transcriptional activator. In these embodiments, transgenic organisms or mixtures of cells that express the chimeric polypeptide contain a second nucleic acid construct that encodes a transcriptional activator. A transcriptional activator is a polypeptide that binds to a DNA site and increases transcription from a promoter. Many transcriptional activators have discrete DNA binding and transcription activation domains. The DNA binding domain(s) and transcription activation domain(s) of transcriptional activators can be synthetic or can be derived from different sources (e.g., two-component system transcriptional activators). In a preferred embodiment, the transcriptional activator is a two-component system transcriptional activator having a transcription activation domain derived from Ga14 and a DNA binding domain derived from VP16. The recognition site for the transcriptional activator polypeptide is positioned with respect to the transcription start site so that the site-bound transcriptional activator polypeptide increases transcription from the promoter that drives transcription of the chimeric polypeptide. The appropriate position of the recognition site relative to the transcription start site varies for different transcriptional activator polypeptides, and those skilled in the art will appreciate where with respect to the transcription start site the recognition site for a particular transcriptional activator needs to be positioned in order to effectively increase transcription. Populations of transgenic organisms or cells having a nucleic acid construct that encodes a chimeric polypeptide and a nucleic acid construct that encodes a transcriptional activator polypeptide can be produced by transformation, transfection, or genetic crossing.

The invention is further described in the following examples, which do not limit the scope of the invention described in the claims.

EXAMPLES

Construction of a chimeric polypeptide.

The pTM plasmid, which contains the coding sequence for the wild type transmembrane polypeptide $AHH_{10}$ (Genbank Accession No. S74033) is digested at the NotI site and the SpeI site. A DNA fragment containing the GFP coding sequence (Genbank Accession No. Afnf3395) is joined to the $AHH_{10}$ DNA fragment at the 3' end to create plasmid pTMReport. The pTMReport plasmid contains the $AHH_{10}$ coding sequence fused in proper reading frame to the GFP coding sequence. The pTMReport plasmid is digested at the EcoRI site, and a DNA fragment containing the FLAG™ coding sequence is inserted in the same reading frame at this site. An Arabidopsis GL2 promoter is inserted at the 5' end of the coding sequence. A nos transcriptional terminator fragment is inserted at the 3' end of the coding sequence, resulting in a plasmid designated pTMReportSort. The pTMReportSort plasmid thus encodes a chimeric polypeptide having transmembrane segments of the $AHH^{10}$ polypeptide, a C-terminal intracellular GFP reporting segment and a FLAG™ sorting segment in an extracellular loop. The GL2 promoter facilitates expression of the chimeric polypeptide in non-root hair cells of the epidermal tissue in Arabidopsis seedlings (Masucci et al. Development 12:1253–1260. 1996.).

Variations of the pTMReportSort plasmid have promoters other than the Arabidopsis GL2 promoter inserted at the 5' end of the $AHH_{10}$ coding sequence. The Arabidopsis FIS2 promoter facilitates expression of the chimeric polypeptide in central cell and polar nuclei inside unfertilized Arabidopsis embryo sacs (Luo et al. PNAS 97:10637–10642. 2000). The corn KNI promoter facilitates expression of the chimeric polypeptide in the shoot apical meristem in corn embryos (Smith et al. Development 116:21-30. 1992). The rice Gt1 promoter facilitates expression of the chimeric polypeptide in the endosperm of rice seeds (Ye et al. Science 287:5451–5455. 2000). The yeast Ime2 promoter facilitates expression of the chimeric polypeptide in sporulating yeast cells (Mai and Breeden. Molecular and Cell Biology 20:478–487. 2000). The mouse Pax2 promoter facilitates expression of the chimeric polypeptide in the optic stalk in mouse retinas (Schwartz et al. Development 127:4325–4334. 2000).

Creating a transgenic organism.

Plasmid pTMReportSort is introduced into Arabidopsis plants by Agrobacterium tumefaciens mediated transformation. See, U.S. Pat. No. 4,940,838; Bechtold, N., et al., C.R. Acad. Sci. Paris, 316:1194–1199 (1993). $R_1$ seedlings are examined at 40× magnification under light having a wavelength of 365 nm to identify those seedlings that express the chimeric polypeptide in specific cells (i.e., seedlings that are visibly fluorescent with respect to root non-hair cells at 10 days after germination).

Similarly, a pTMReportSort variant having an Arabidopsis FIS2 promoter is introduced into Arabidopsis plants by Agrobacterium tumefaciens mediated transformation. See, U.S. Pat. No. 4,940,838; Bechtold, N., et al., C.R. Acad. Sci. Paris, 316:1194–1199 (1993). $R_1$ plants are examined at 40× magnification under light having a wavelength of 365 nm to identify those seedlings that express the chimeric polypeptide in specific cells (i.e., plants that are visibly fluorescent with respect to the central cell and polar nuclei within unfertilized embryo sacs).

A pTMReportSort variant having a corn KNI promoter is introduced into corn plants by Agrobacterium tumefaciens mediated transformation. See, U.S. Pat. No. 5,591,616. $R_1$ seedlings are examined at 40× magnification under light having a wavelength of 365 nm to identify those seedlings that express the chimeric polypeptide in specific cells (i.e., seedlings that are visibly fluorescent with respect to the shoot apical meristem).

A pTMReportSort variant having a rice Gt1 promoter is introduced into rice plants. See, U.S. Pat. No. 5,591,616. $R_1$ plants are examined at 40× magnification under light having a wavelength of 365 nm to identify those seedlings that express the chimeric polypeptide in specific cells (i.e., plants that are visibly fluorescent with respect to the seed endosperm).

A pTMReportSort variant having a yeast Ime2 promoter is introduced into yeast by LiAc/SS-DNA/PEG transformation. See, Gietz, R. D. and R. A Woods (1998). Transformation of yeast by the lithium acetate/single-stranded carrier DNA/PEG method. In: Methods in Microbiology 26. Eds. A. J. P Brown and M. F. Tuite. Academic Press, New York. Transformants are examined at 40× magnification under light having a wavelength of 365 nm to identify those that express the chimeric polypeptide in specific cells (i.e., transformants that are visibly fluorescent during sporulation).

A pTMReportSort variant having a mouse Pax2 promoter is introduced into mice by nuclear cloning. See, Rideout et al. Nature Genetics 24:109-10. 2000. Transformants are examined at 40× magnification under light having a wavelength of 365 nm to identify those individuals that express the chimeric polypeptide in specific cells (i.e., transformants that are visibly fluorescent with respect to the retinal optic stalk).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A chimeric polypeptide comprising:
   a) at least one transmembrane segment derived from the group consisting of bacteriorhodopsin, photosynthetic reaction center L- and M-chains, and Cry δ endotoxin;
   b) a sorting segment within an extracellular domain of said chimeric polypeptide, said sorting segment positioned at other than the amino terminus of said chimeric polypeptide; and
   c) an intracellular reporting segment.

2. The chimeric polypeptide of claim 1, wherein said chimeric polypeptide comprises at least two transmembrane segments, and wherein said extracellular domain is an extracellular loop.

3. The chimeric polypeptide of claim 1 wherein said sorting segment is selected from the group consisting of c-myc, FLAG, 6xHIS, and Hemagglutinin.

4. The chimeric polypeptide of claim 1 wherein said sorting segment is selected from the group consisting of avidin and streptavidin.

5. The chimeric polypeptide of claim 1 wherein said reporting segment is bioluminescent.

6. The chimeric polypeptide of claim 5 wherein said reporting segment fluoresces upon exposure to ultraviolet or visible light having a wavelength between 300 nm and 600 nm.

7. The chimeric polypeptide of claim 6 wherein said reporting segment is selected from the group consisting of amFP486, asFP600, cFP484, dgFP512, dmFP592, drFP583, drFP583/dmFP592, dsFP483, zFP506, zFP538, GFP, GFPuv, GFPmutl, EGFP, ECFP, EYFP, EBFP, BFP2, d4EGFP, d2EGFP, d1EGFP, d4EGFP, DsRed, and DsRed1.

8. The chimeric polypeptide of claim 1 wherein said reporting segment is capable of enzymatic catalysis.

9. The chimeric polypeptide of claim 1 wherein said reporting segment is positioned at the carboxy terminus of said chimeric polypeptide.

10. The chimeric polypeptide of claim 1 wherein said reporting segment is positioned at the amino terminus of said chimeric polypeptide.

11. A cell containing a chimeric polypeptide, said chimeric polypeptide comprising:
    a) at least one transmembrane segment derived from the group consisting of bacteriorhodopsin, photosynthetic reaction center L- and M-chains, and Cry δ endotoxin;
    b) a sorting segment within an extracellular domain of said chimeric polypeptide, said sorting segment positioned at other than the amino terminus of said chimeric polypeptide; and
    c) an intracellular reporting segment.

12. A cell containing the nucleic acid of claim 11.

13. A nucleic acid construct comprising a coding sequence operably linked to a promoter, wherein said coding sequence encodes a chimeric polypeptide comprising:
    a) at least one transmembrane segment derived from the group consisting of bacteriorhodopsin, photosynthetic reaction center L- and M-chains, and CrY δ endotoxin;
    b) a sorting segment within an extracellular domain of said chimeric polypeptide, said sorting segment positioned at other than the amino terminus of said chimeric polypeptide; and
    c) an intracellular reporting segment.

14. A cell containing the nucleic acid construct of claim 13.

* * * * *

UNITED STATES PATENT AND TRADEMARK OFFICE
CERTIFICATE OF CORRECTION

| | | |
|---|---|---|
| PATENT NO. | : 6,977,293 B1 | Page 1 of 1 |
| APPLICATION NO. | : 10/046660 | |
| DATED | : December 20, 2005 | |
| INVENTOR(S) | : Roger I. Pennell | |

It is certified that error appears in the above-identified patent and that said Letters Patent is hereby corrected as shown below:

Title Page, References Cited, Other Publications, Hirasawa et al. reference, after "Adrenoceptors" please insert --chlorethylclonidine preferentially alkylates the accessible cell surface α1-adrenoreceptors--;

Title Page (Page 2), References Cited, Other Publications, Yellin et al. reference, please delete "Yellin" and insert --Yelin--therefor;

Column 9, line 5, please delete "δendotoxin" and insert --δ endotoxin--therefor;

Column 10, line 7, please delete "cell containing" and insert --nucleic acid encoding-- therefor;

Column 10, line 25, please delete "CrY" and insert --Cry--therefor.

Signed and Sealed this

Eighteenth Day of July, 2006

JON W. DUDAS
*Director of the United States Patent and Trademark Office*